United States Patent [19]
Beauvais et al.

[11] Patent Number: 5,876,379
[45] Date of Patent: Mar. 2, 1999

[54] SYRINGE CANNULA HOLDER

[75] Inventors: Charles K. Beauvais, Sinking Spring; Edwin W. Blatt, Denver, both of Pa.

[73] Assignee: Alcon Laboratories, Inc., Fort Worth, Tex.

[21] Appl. No.: 12,128

[22] Filed: Jan. 22, 1998

[51] Int. Cl.[6] ................................................. A61M 5/00
[52] U.S. Cl. ........................ 604/181; 604/241; 604/264
[58] Field of Search ................................. 604/181, 187, 604/188, 218, 239, 240, 241, 264, 272, 232; 600/5

[56] References Cited

U.S. PATENT DOCUMENTS

| | | |
|---|---|---|
| 609,982 | 8/1898 | Winchester . |
| 1,012,700 | 12/1911 | Payne . |
| 1,157,552 | 10/1915 | Kispert . |
| 2,020,111 | 11/1935 | Eisele . |
| 2,806,473 | 9/1957 | Lingley . |
| 3,076,455 | 2/1963 | McConnaughey et al. . |
| 3,583,399 | 6/1971 | Ritsky . |
| 3,811,441 | 5/1974 | Sarnoff . |
| 3,895,633 | 7/1975 | Bartner et al. . |
| 4,112,945 | 9/1978 | Helixon et al. . |
| 4,122,836 | 10/1978 | Burnett . |
| 4,540,405 | 9/1985 | Miller et al. . |
| 4,592,746 | 6/1986 | Ewalt et al. . |
| 4,610,672 | 9/1986 | Burkholder et al. . |
| 4,994,045 | 2/1991 | Ranford . |
| 5,360,409 | 11/1994 | Boyd, III et al. ........................ 604/198 |
| 5,419,775 | 5/1995 | Haffner et al. . |
| 5,828,073 | 10/1998 | Zhu et al. ............................ 250/506.1 |

*Primary Examiner*—John D. Yasko
*Assistant Examiner*—Michael I. Hayes
*Attorney, Agent, or Firm*—Jeffrey S. Schira

[57] ABSTRACT

A syringe cannula holder having an outer sleeve with an external thread that receives an internally threaded nut. The nut has a passage that permits a syringe cannula to pass through so that when the syringe body is installed within the outer sleeve, the nut may be threaded onto the outer sleeve leaving the cannula exposed. The syringe is held within the outer sleeve by a retaining ring.

6 Claims, 5 Drawing Sheets

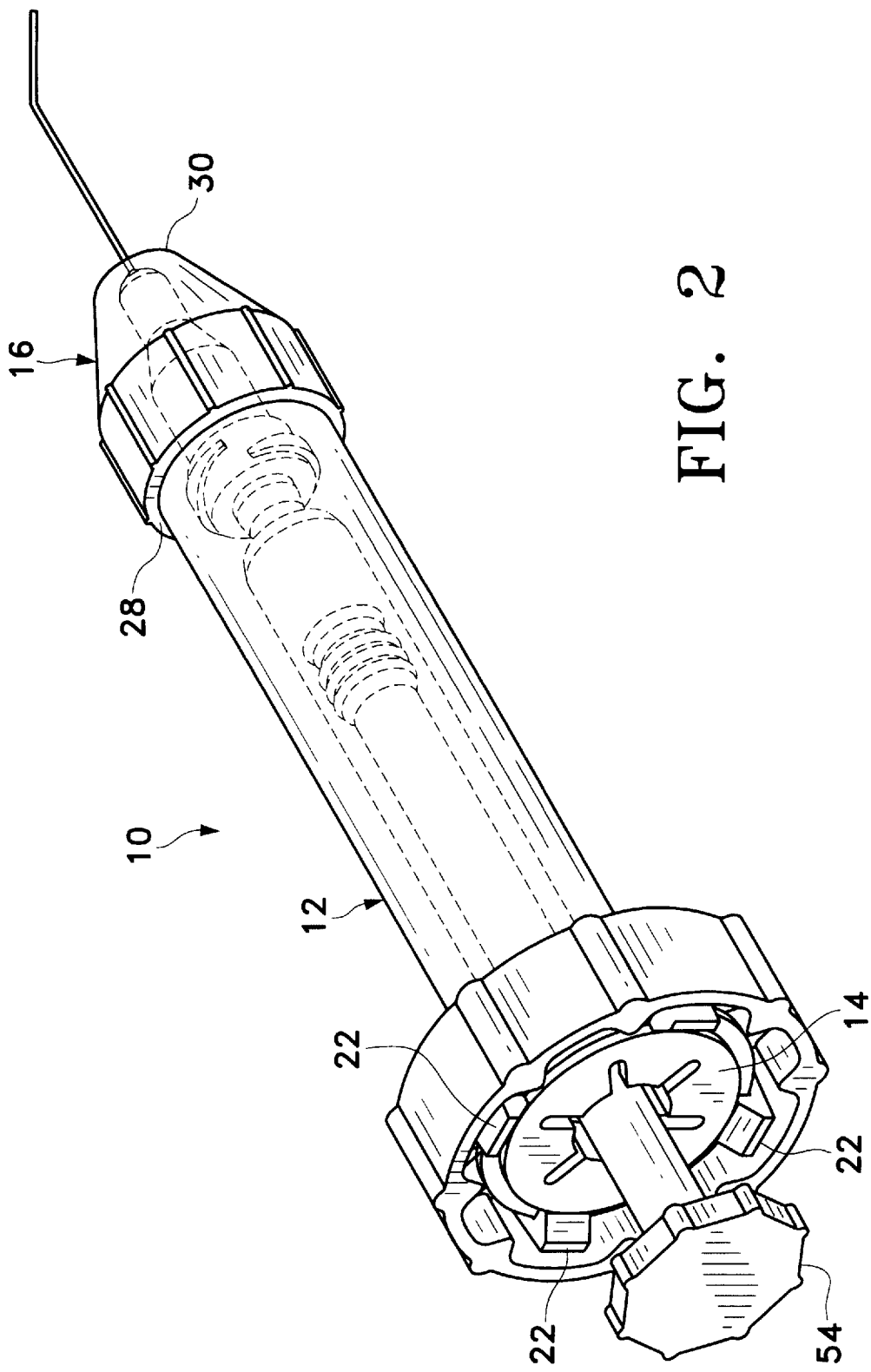

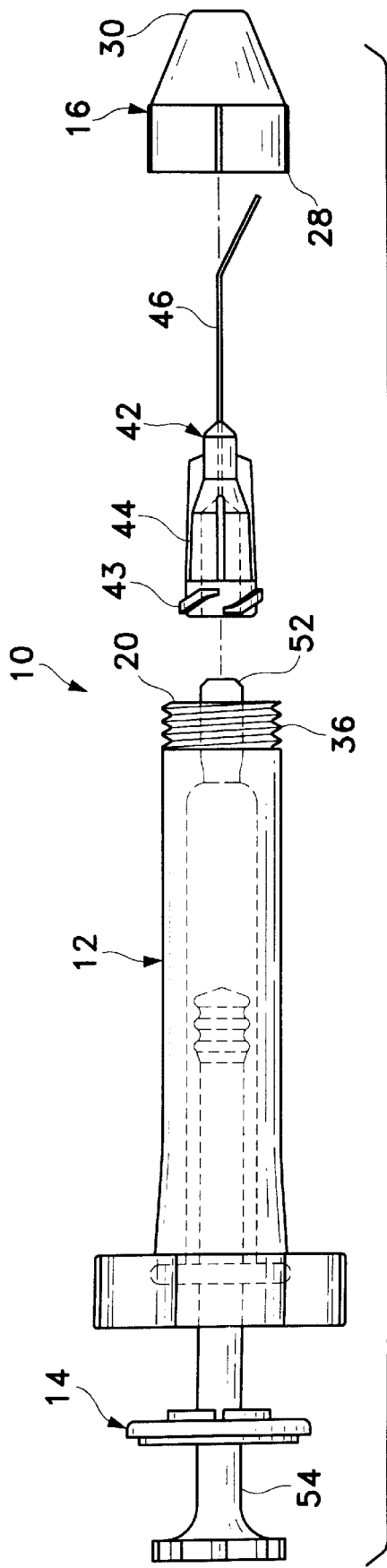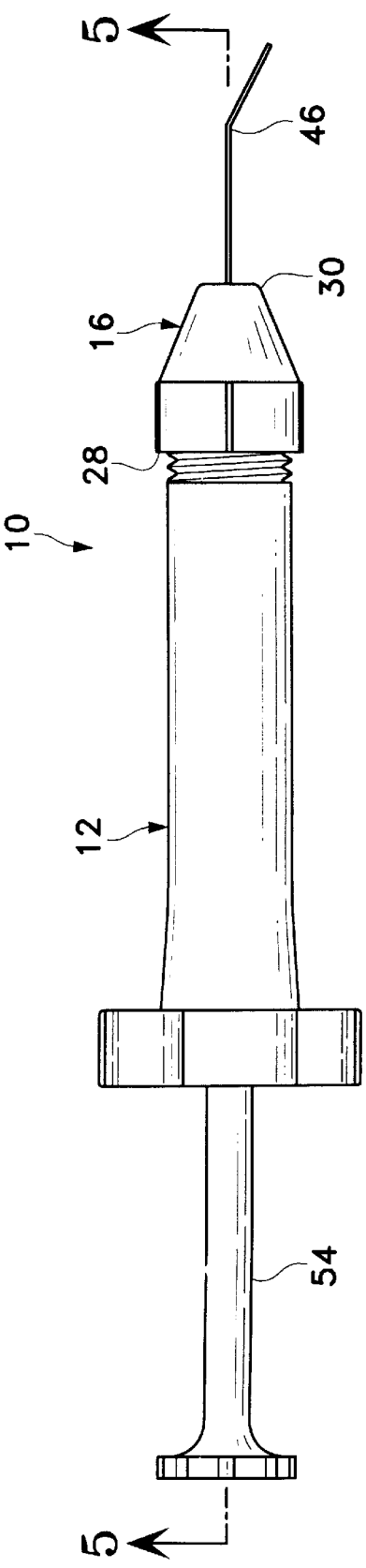

SYRINGE CANNULA HOLDER

BACKGROUND OF THE INVENTION

This invention relates generally to the field of syringes and, more particularly, to syringes used with viscoelastic agents.

During surgery, particularly ophthalmic surgery, various viscoelastic agents may be introduced into the surgical site. These agents generally are expressed into the surgical site out of a syringe and through a relatively thin cannula. The pressure at the syringe/cannula fitting can be very high due to the high viscosity of the viscoelastic agents. As a result, attempts to express the agent out of the cannula can cause the cannula to become disconnected from the syringe.

Prior art syringes intended for use with viscoelastic agents, such as described in U.S. Pat. No. 4,540,405 (Miller, et al.) have been directed primarily at providing a better grip on the relatively small syringe so that sufficient force can be applied to express the viscoelastic agent, and the cannula may still become disconnected from the syringe.

Accordingly, a need continues to exist for a holder that tightly secures a cannula on the end of a syringe.

BRIEF SUMMARY OF THE INVENTION

The present invention improves upon the prior art syringe and/or cannula holders by providing a holder having an outer sleeve with an external thread that receives an internally threaded nut. The nut has a passage that permits a syringe cannula to pass through so that when the syringe body is installed within the outer sleeve, the nut may be threaded onto the outer sleeve leaving the cannula exposed. The syringe is held within the outer sleeve by a retaining ring.

Accordingly, one objective of the present invention is to provide a cannula holder that helps to prevent the cannula from disconnecting from the syringe during use.

Another objective of the present invention is to provide a syringe sleeve having an external thread that receives an internally threaded nut.

This and other advantages and objectives of the present invention will become apparent from the detailed description and claims that follow.

BRIEF DESCRIPTION OF THE DRAWINGS

FIG. 2 is a perspective view of the cannula holder of the present invention with the syringe shown in shadow line.

FIG. 3 is an expanded elevational view of the cannula holder of the present invention receiving a cannula and a locking nut, with the syringe shown in shadow line.

FIG. 4 is a elevational view of the cannula holder of the present invention.

DETAILED DESCRIPTION OF THE INVENTION

Figure 1:
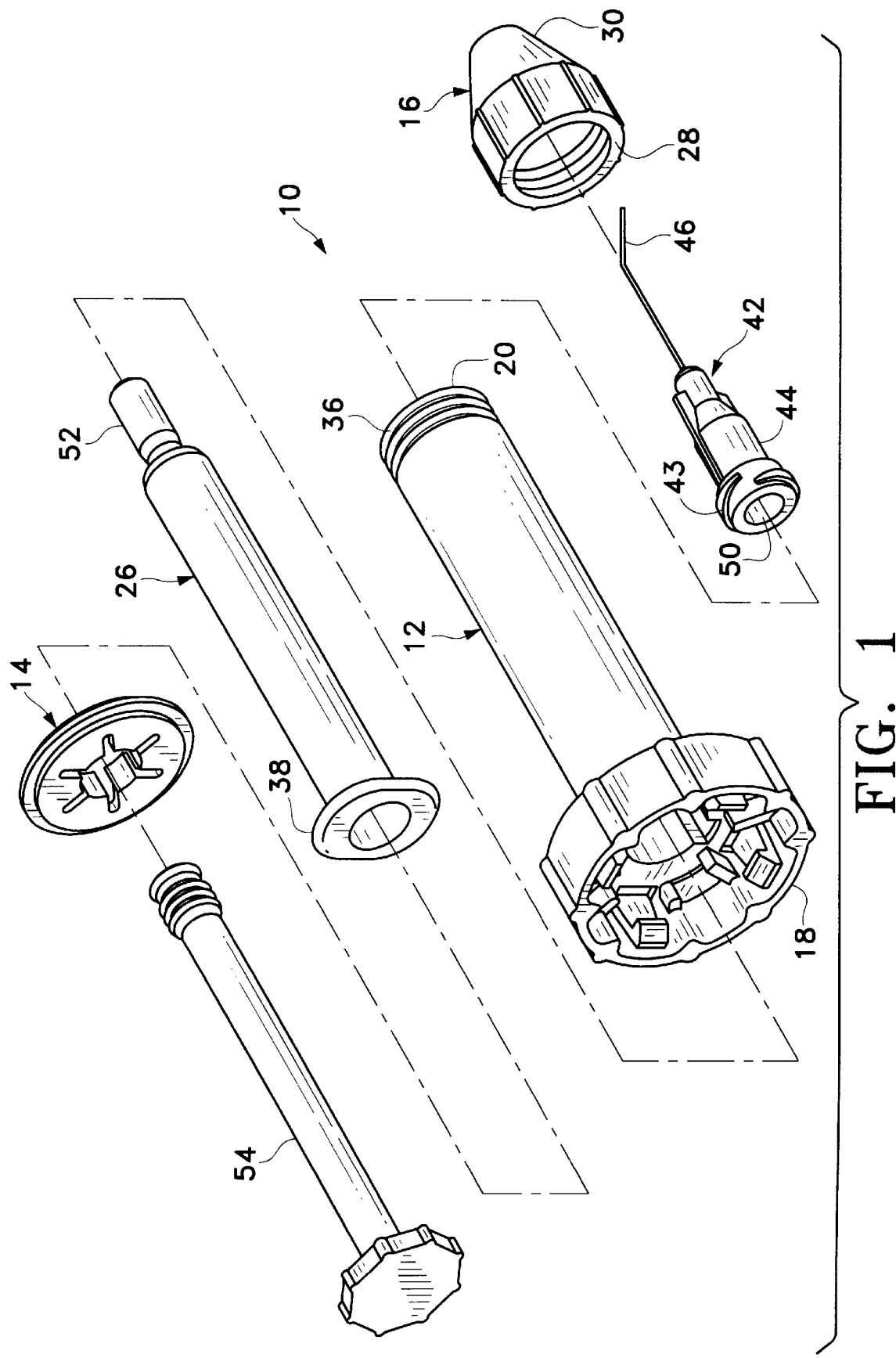
FIG. 1 is an expanded perspective view of the cannula holder of the present invention receiving a syringe and cannula.
Figures 8, 9, 10:
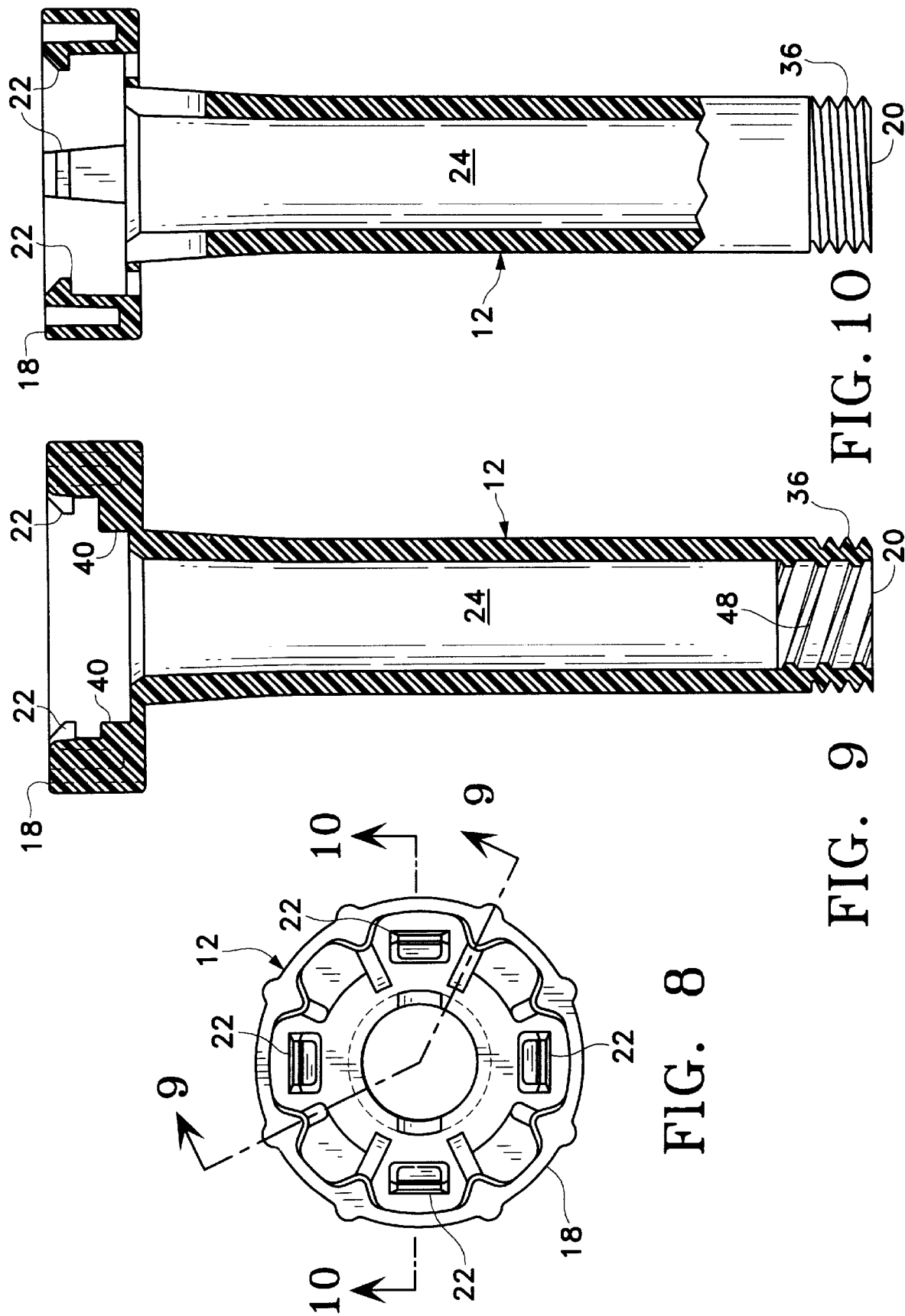
FIG. 8 is a rear end view of a syringe sleeve that may be used with the present invention.
FIG. 9 is a cross-sectional view of a syringe sleeve that may be used with the present invention taken along line 9—9 in FIG. 8.
FIG. 10 is a cross-sectional view of a syringe sleeve that may be used with the present invention taken along line 10—10 in FIG. 8.

As best seen in FIG. 1, syringe cannula holder 10 of the present invention generally consists of outer sleeve 12, syringe retainer 14 and locking nut 16. As best seen in FIGS. 8–10, sleeve 12 is generally tubular with flared end 18 and internally and externally threaded end 20 opposite end 18. Flared end 18 contains snap tabs 22 that project into bore 24. Sleeve 12 is sized and shaped to accept any commercially available syringe 26 and may be made of any suitable material, such as plastic, with polycarbonate being preferred.

Figure 5:
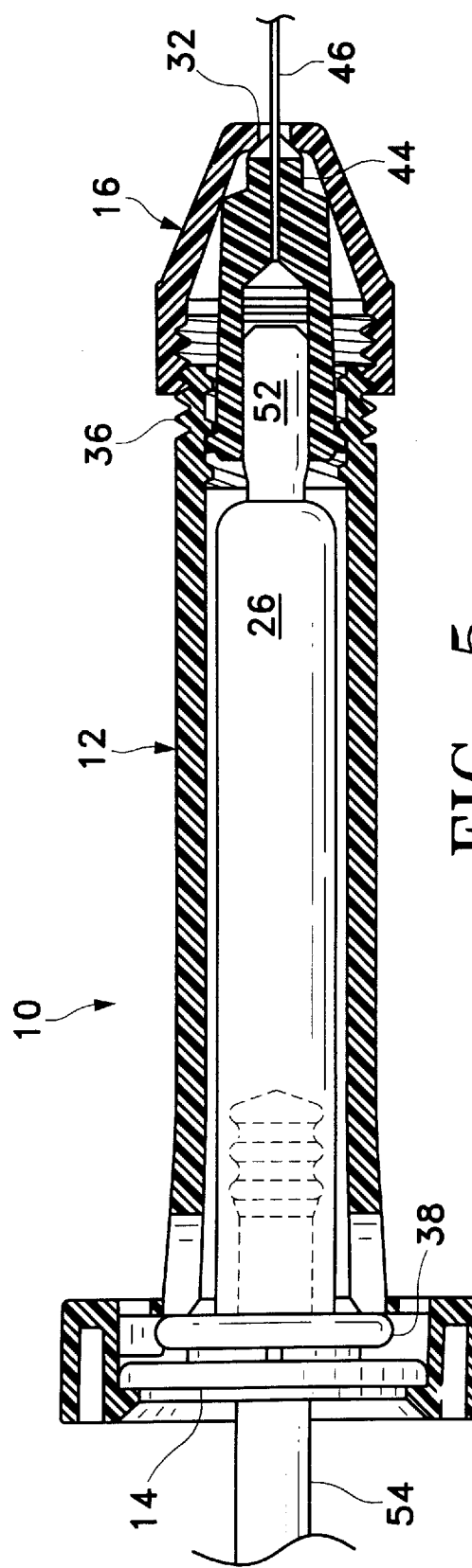
FIG. 5 is a cross-sectional view of the cannula holder of the present invention taken along line 5—5 in FIG. 4.
Figure 7:
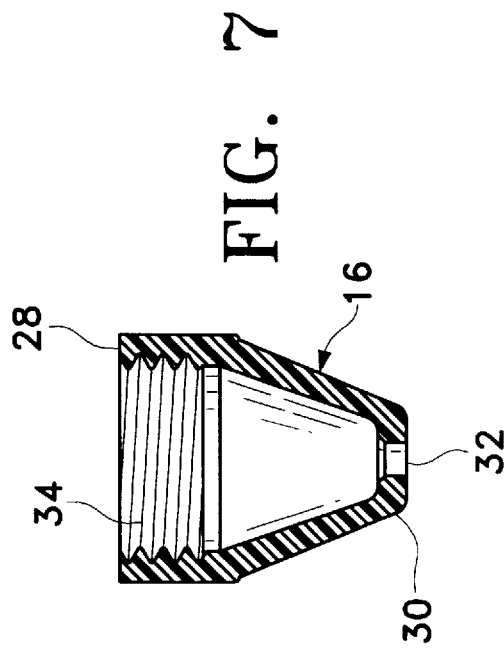
FIG. 7 is a cross-sectional view of a locking nut that may be used with the present invention taken along line 7—7 in FIG. 6.
Figure 6:
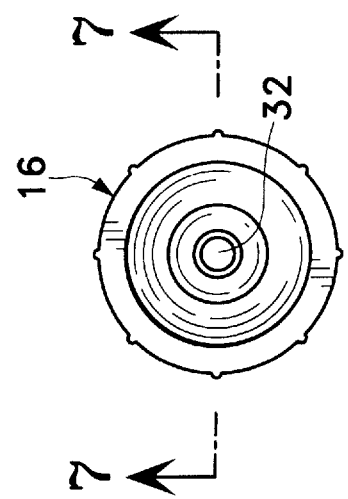
FIG. 6 is a front end view of a locking nut that may be used with the present invention.

As best seen in FIGS. 5–7, locking nut 16 has an open, internally threaded end 28, and a generally closed, tapered end 30 containing small opening 32. Open end 28 and internal thread 34 are sized and shaped to be received on external thread 36 on end 20 of sleeve 12 and may be made of any suitable material, such as plastic, with polycarbonate being preferred.

As best seen in FIGS. 1, 3 and 5, in use, plunger 54 is inserted into syringe 26 and the plunger/syringe is inserted into bore 24 of sleeve 12. Flange 38 on syringe 26 fits within recess 40 in end 18 of bore 24 and held in place by snapping retainer 14 over flange 38 and under snaps 22 on sleeve 12. Cannula assembly 42 is inserted into end 20 of sleeve 12 and rotated so that external thread 43 on cannula hub 44 is received within internal thread 48 on end 20 of sleeve 12 and bore 50 on hub 44 is frictionally received on end 52 of syringe 26. Opening 32 on locking nut 16 is threaded over cannula 46 on cannula assembly 42 so that internal thread 34 on locking nut 16 engages external thread 36 on end 20 of sleeve 12. Locking nut 16 is turned until locking nut 16 is tight against cannula hub 44, as best seen in FIG. 5.

This description is given for purposes of illustration and explanation. It will be apparent to those skilled in the relevant art that modifications may be made to the invention as herein described without departing from its scope or spirit.

We claim:

1. A cannula holder for a syringe, comprising:
    a) a sleeve having a bore for receiving a syringe having a flange, the sleeve having an open, flared end and an end having an external thread opposite the flared end;
    b) a retaining nut having an internal thread sized and shaped to be received on the external thread of the sleeve; and
    c) a retainer sized and shaped to fit within the open, flared end of the sleeve and over the syringe flange for retaining the syringe within the sleeve.

2. The cannula holder of claim 1 wherein the sleeve comprises plastic.

3. The cannula holder of claim 1 further comprising a cannula assembly having an external thread that engages an internal thread on the end of sleeve.

4. The cannula holder of claim 3 wherein the retaining nut has a bore and the cannula assembly has an attached cannula projecting outward from the cannula holder so that the cannula is received through the bore on the retaining nut when the retaining nut is received on the end of the sleeve.

5. A cannula holder for a syringe, comprising:
a) a sleeve having a bore for receiving a syringe having a flange, the sleeve having an open, flared end and an end having external and internal threads opposite the flared end;
b) a retaining nut having a bore and an internal thread sized and shaped to be received on the external thread of the sleeve;
c) a cannula assembly having an external thread that engages the internal thread on the end of sleeve; and
d) a retainer sized and shaped to fit within the open, flared end of the sleeve and over the syringe flange for retaining the syringe within the sleeve.

6. The cannula holder of claim 5 wherein the cannula assembly has an attached cannula projecting outward from the cannula holder so that the cannula is received through the bore on the retaining nut when the retaining nut is received on the external thread of the sleeve.

* * * * *